US011650179B2

(12) United States Patent
Klemm

(10) Patent No.: US 11,650,179 B2
(45) Date of Patent: May 16, 2023

(54) ANALYTE MEASUREMENT DEVICE

(71) Applicant: SANOFI, Paris (FR)

(72) Inventor: Thomas Klemm, Frankfurt am Main (DE)

(73) Assignee: Sanofi, Paris (FR)

( * ) Notice: Subject to any disclaimer, the term of this patent is extended or adjusted under 35 U.S.C. 154(b) by 382 days.

(21) Appl. No.: 16/757,104

(22) PCT Filed: Oct. 19, 2018

(86) PCT No.: PCT/EP2018/078686
§ 371 (c)(1),
(2) Date: Apr. 17, 2020

(87) PCT Pub. No.: WO2019/077099
PCT Pub. Date: Apr. 25, 2019

(65) Prior Publication Data
US 2020/0249193 A1    Aug. 6, 2020

(30) Foreign Application Priority Data
Oct. 19, 2017  (EP) ..................................... 17306417

(51) Int. Cl.
G01N 27/327 (2006.01)
G01N 33/49 (2006.01)
(52) U.S. Cl.
CPC ..... *G01N 27/3274* (2013.01); *G01N 27/3275* (2013.01); *G01N 33/49* (2013.01)
(58) Field of Classification Search
CPC ................... G01N 27/327–3278; G01N 33/49
See application file for complete search history.

(56) References Cited

U.S. PATENT DOCUMENTS

2006/0011493 A1   1/2006  Kontschieder et al.
2012/0262298 A1  10/2012  Bohm et al.
(Continued)

FOREIGN PATENT DOCUMENTS

AU    2015200285       2/2015
CN    104132967 A  *  11/2014  ............. G01N 27/04
(Continued)

OTHER PUBLICATIONS

Hui et al., "Quantitative Rapid Analysis Method for Ofloxacin in Raw Milk Based on Molecule-Specific Recognition and Electrochemical Impedance Spectrum," Transactions s of the ASABE (American Society of Agricultural and Biological Engineers) 60(5):1439-1443 Jan. 2017 (Year: 2017).*
(Continued)

*Primary Examiner* — Alexander S Noguerola
(74) *Attorney, Agent, or Firm* — Fish & Richardson P.C.

(57) ABSTRACT

Analyte measurement devices and methods of measuring an analyte in a sample. At least one of the methods include: applying an electrical analysis signal to the sample during a measurement time interval (MT), wherein the electrical analysis signal, when transferred into a frequency space, comprises a superposition of two or more non-zero frequency components at least at a sampling time; measuring at least one electrical response signal from the sample; analyzing the electrical response signal; and determining the amount of the analyte in the sample based on the analyzing.

20 Claims, 5 Drawing Sheets

(56) References Cited

U.S. PATENT DOCUMENTS

| | | | |
|---|---|---|---|
| 2014/0005508 A1 | 1/2014 | Estes et al. | |
| 2015/0025778 A1 | 1/2015 | Matsuoka et al. | |
| 2016/0011140 A1* | 1/2016 | Buck, Jr. ............ | G01N 27/3274 205/777.5 |

FOREIGN PATENT DOCUMENTS

| | | |
|---|---|---|
| JP | S60-236058 | 11/1985 |
| JP | H06-048204 | 6/1994 |
| JP | 2003-511694 | 3/2003 |
| JP | 2004-085566 | 3/2004 |
| JP | 2013-516599 | 5/2013 |
| JP | 2013-516615 | 5/2013 |
| JP | 2013-178227 | 9/2013 |
| JP | 2016-224075 | 12/2016 |
| WO | WO 2003/060154 | 7/2003 |
| WO | WO 2011/078838 | 6/2011 |
| WO | WO 2011/079938 | 7/2011 |
| WO | WO 2011/082820 | 7/2011 |

OTHER PUBLICATIONS

EPO computer-generated English language translation of Kang et al. CN 104132967 A (Year: 2014).*

Swarthmore online "Fourier Xform of Periodic Functions" downloaded Oct. 6, 2022 fhttps://Ipsa.swarthmore.edu/Fourier/Xforms/FXPeriodic.html#:~:text=Example%3A%20Fourier%20Transform%20of%20Square%20Wave,-Consider%20the%20periodic&text=The%20shape%20of%20the%20transform,(and%20amplitude%202%CF%80cn). (Year: 2022).*

Swarthmore online "Fourier Series Examples" downloaded Oct. 6, 2022 https://Ipsa.swarthmore.edu/Fourier/Series/ExFS.html (Year: 2022).*

Gavin Teague, "Mass flow measurement of multi-phase mixtures by means of tomographic techniques", Doctoral dissertation, University of Capetown, 224 pages, 2002.

PCT International Preliminary Report on Patentability in Application No. PCT/EP2018/078686, dated Apr. 21, 2020, 6 pages.

PCT International Search Report and Written Opinion in Application No. PCT/EP2018/078686, dated Jan. 1, 2019, 9 pages.

* cited by examiner

ANALYTE MEASUREMENT DEVICE

CROSS REFERENCE TO RELATED APPLICATIONS

The present application is the national stage entry of International Patent Application No. PCT/EP2018/078686, filed on Oct. 19, 2018, and claims priority to Application No. EP 17306417.1, filed on Oct. 19, 2017, the disclosures of which are incorporated herein by reference.

TECHNICAL FIELD

The present disclosure relates to an analyte measurement device and to a method of measuring an analyte in a sample, in particular in a liquid sample. In one aspect, the disclosure relates to the field of blood glucose monitoring (BGM), and in particular, to the measuring and monitoring of blood glucose in a sample of blood.

BACKGROUND

Blood glucose monitoring is a way of testing the concentration of glucose in the blood. Particularly important in the care of diabetes mellitus, a blood glucose test is performed by piercing the skin, typically, on the finger, to draw blood, then applying the blood to a chemically active disposable test strip. Different manufacturers may use different technologies, but some systems measure an electrical characteristic, and use this to determine the glucose level in the blood.

Healthcare professionals advise patients with diabetes on the appropriate monitoring regimen for their condition. Most people with Type 2 diabetes test at least once per day. Diabetics who use insulin usually test their blood glucose more often, e.g. 3 to 10 times per day, both to assess the effectiveness of their prior insulin dose and to help determine their next insulin dose. Improved technology for measuring blood glucose is rapidly changing the standards of care for all patients suffering diabetes.

Some methods and devices for monitoring a blood glucose level use test strips that are provided with glucose biosensors. For instance, test strips have been suggested that comprise amperometric enzyme electrodes, based on glucose oxidase (GOx). During a chemical reaction, i.e. during the glucose oxidase, glucose and oxygen convert into gluconic acid and water.

Known amperometric test strips exploit enzymes to convert the analyte of interest, e.g. glucose, into an electrical current. These biosensors are mainly based on an enzyme class called oxidases, that may catalyze the transfer of electrons between two molecules according to the following steps. In a first step, the enzyme binds molecular oxygen and the target compound into its active site and oxidizes the analyte, extracting two electrons in the process. During the oxidation, the electrons are collected by the enzyme's cofactor, which enters in a reduced state. In a further stage the enzyme's cofactor returns to its native state by transferring the electron to a molecule of oxygen and generating hydrogen peroxide as a product allowing a new cycle to start.

The measurement of hydrogen peroxide by chronoamperometry may be highly influenced by the concentration of oxygen in the sample. Some test strips solve this problem by integrating into their composition a mediator, i.e. a chemical compound acting as an electron shuttle between the enzyme's cofactor and the electrode.

Implementations of the present disclosure can provide an improved method of measuring an analyte in a sample and provide an improved analyte measurement device for measuring such an analyte or several analytes in a sample.

SUMMARY

In one aspect there is provided a method of measuring and analyte in a sample. The method comprises the steps of applying an electrical analysis signal to the sample during a measurement time interval. The electrical analysis signal, when transferred into a frequency space, comprises a superposition of two or more non-zero frequency components at least at a sampling time. The method further comprises the step of measuring of at least one electrical response signal from the sample in response to the application of the electrical analysis signal to the sample. Thereafter and in a further step the electrical response signal is analyzed. Based on the analysis of the electrical response signal an amount, a quantity or a concentration of the analyte in the sample is determined.

Since the electrical analysis signal when applied to the sample comprises two or more non-zero frequency components at a given sampling time the sample is exposed to at least two frequency components simultaneously. The electrical response signal derivable from the sample in return can be spectrally analyzed. The electrical response signal therefore also comprises a superposition of at least two non-zero frequency components that are indicative of at least one analyte contained in the sample. In this way and by following this multiple frequency component approach the precision of the electrochemical analysis of the sample can be improved. At a given sample time the sample is exposed to at least two different frequency components of an electrical analysis signal. The electrical response signal can be spectrally analyzed with regards to at least two frequency components. In this way a kind of an electrochemical impedance spectroscopy is applied to the sample for analyte measurement.

It is of particular benefit that a substantially non-varying electrical analysis signal can repeatedly and/or regularly applied to the sample. The respective electrical response signal obtainable from the sample or modified by the sample can then be analyzed differently, e.g. with regard to different spectral ranges or different frequency components. This may have a practical benefit since the sample, e.g. a test strip with a blood sample, is repeatedly exposed to unmodified and non-varying electrical analysis signals. Modifications of the sample over time or modifications and a temporal behavior of the electrochemical reaction taking place in or on the sample can thus be repeatedly monitored and measured under constant and unmodified measurement conditions.

It is even conceivable to constantly apply the electrical analysis signal to the sample, hence to apply the electrical analysis signal to the sample in continues mode or in a cw mode. Independent of the type of application of the electrical analysis signal to the sample spectral ranges of the electrical response signal can be separately analyzed by respective analyzing hardware and software without affecting the sample.

It is particularly conceivable, that during a measurement time interval numerous and a sequence of electrical analysis signals are repeatedly applied to the sample and that for each application of an electrical analysis signal to the sample there is measured at least one electrical response signal from the sample in return. During the measurement time, the sample is subject to an electrochemical reaction that is monitored over time. The measurement time interval may typically range between 2 to 10 seconds. It may range between 4 to 6 seconds. In some typical examples, the measurement time interval may last about 5 seconds.

According to an example, the electrical analysis signal comprises a noise signal comprising one of a white noise frequency spectrum, a pink noise frequency spectrum, a red noise frequency spectrum, a blue noise frequency spectrum, a violet noise frequency spectrum and a grey noise frequency spectrum. The noise signal may be constantly and permanently applied to the sample over the entire measurement time interval. Alternatively, the noise signal may be applied repeatedly at least during selected sampling times within the measurement time interval.

The noise signal comprises a superposition of a multitude of frequency components, wherein each frequency component may be subject to temporal variations or fluctuations. It is even conceivable, that the noise signal comprises an infinitesimal number of different frequency components. In this way, the sample is simultaneously exposed to a large number or even to an infinitesimal number of different frequency components. The electrical response signal obtainable from the sample in return thus carries a respective amount of frequency components that can be selectively and subsequently analyzed for determining the amount or the quantity of the analyte in the sample.

In particular, the noise signal comprises a pink noise frequency spectrum. The pink noise signal comprises a frequency spectrum such that the power spectral density, i.e. the energy or power per frequency interval is inversely proportional to the frequency of the signal. With a pink noise signal, each octave, i.e. halving/doubling in frequency, carries an equal amount of noise energy. The noise signal and in particular the pink noise signal may comprise a frequency range in the region from 10 Hz to 20 kHz.

When the electrical analysis signal comprises a noise signal or when the electrical analysis signal conditions of a noise signal, e.g. a pink noise signal consists of a noise signal, in particular of a pink noise signal almost any conceivable frequency component is contained in the electrical analysis signal and the sample is excited or exposed to almost any conceivable frequency components. It is then that also the electrical response signal carries a multitude of frequency components.

For analyzing the electrical response signal a suitable or a predetermined frequency spectrum of the electrical response signal can be filtered and can be separately analyzed. Such a filtering, selection or limitation to only one or to several frequency components of the electrical response signal is entirely conducted on the analysis side and leaves the excitation or exposure of the sample with the electrical analysis signal unchanged. The measurement conditions as seen from the sample remain non-amended and unchanged, thus enabling to increase the measurement precision and to improve the reproducibility of the measurement.

According to another example, the electrical response signal is filtered by a variable bandpass filter having a center frequency that is varied during the measurement time interval. A portion of the electrical response signal that passes the variable bandpass filter is analyzed for determining the amount of the analyte in the sample. By means of a variable bandpass filter, only one or several predetermined frequency components of the electrical response signal can be selected for signal analysis and for the determination of the amount, the quantity or the concentration of the analyte.

A variable bandpass filter can be dynamically tuned or adjusted within a comparatively short time. In this way, numerous different frequency components can be filtered from the electrical response signal only by the varying the center frequency of the variable bandpass filter during the measurement time interval. Switching or modifying of the center frequency of the variable bandpass filter can be conducted in a few milliseconds, such as 10 ms or even less. In this way, a rather high sampling rate, e.g. in the range of 100 samples per second can be provided. The center frequency of the variable bandpass filter can be modified and varied in accordance to a predefined sampling interval, such as 10 ms or even less. The sampling interval, hence the time interval between two consecutive sampling times, is only governed and limited by the dynamic behavior and the dynamic switching characteristics of the variable bandpass filter.

According to another example, at a first sampling time the variable bandpass filter is tuned to a first center frequency. At a second sampling time the variable bandpass filter is tuned at least to a second center frequency. The first center frequency and the second center frequency are different. Moreover, after each sampling interval, the center frequency of the bandpass filter is switched or tuned to a different center frequency. It is conceivable that the center frequency of the bandpass filter is monotonically increased or decreased step by step at each sampling time.

Once a maximum center frequency has been reached, the center frequency may decrease step-by-step, or may be abruptly switched to a minimum center frequency. Once a minimum center frequency has been reached, the center frequency may increase step-by-step, or may be abruptly switched to a maximum center frequency.

It is conceivable that the variable bandpass filter is consecutively tuned or switched to 10 different center frequencies, 50 different center frequencies, or even hundred or hundreds of different center frequencies. In this way, the electrical response signal can be analyzed with regard to a respective number of different frequency components. By applying a noise signal as the electrical analysis signal to the sample, a selection of particular center frequency can be exclusively implemented by software and does not require a modification of a hardware setup of a respective analyte measurement device.

Moreover, the number of frequency components, as well as the center frequencies of the variable bandpass filter, can be easily modified by operating and controlling the variable bandpass filter accordingly. It is even conceivable to modify the number of frequency components and/or the selection of frequency components to be analyzed during the measurement time interval. In this way, the method may dynamically react on specific of a varying measurement conditions.

According to a further example, the variable bandpass filter is repeatedly tuned to the first center frequency and to the second center frequency during the measurement time interval. There may be conducted numerous measurement cycles during the measurement time interval, wherein during each measurement cycle each of the predefined center frequencies or frequency components has been selected once. As an example, and when, for instance 10 different frequency components are selected for the analysis of the electrical response signal and with a sampling interval of 10 ms, a measurement cycle may last 100 ms. During a measurement time interval of 5 seconds, the method and a respective analyte measurement device may conduct 50 measurement cycles, and may thus collect 50 electrical response signals for each one of the 10 frequency components.

According to another example, the electrical analysis signal comprises a sequence of pulses, wherein a single pulse of the sequence of pulses comprises a peak-shaped pulse or a rectangular-shaped pulse. Other pulse forms are also conceivable. Consecutive pulses are applied to the sample at a predefined repetition rate. The repetition rate of the sequence of pulses may be in a range of a few milliseconds, e.g. in a range of 10 ms or less.

Between two consecutive pulses of the sequence of pulses the electrical analysis signal may comprise a zero amplitude or a constant amplitude. Typically, the electrical response signal is analyzed during pulse-pauses that follow a pulse of the electrical analysis signal. In this way, a dynamic response of the sample can be analyzed over time. The electrical response signal following a pulse of the electrical analysis signal may be denoted as a pulse reply signal. The pulse reply signal may be indicative of the amount, the quantity and/or concentration of the analyte in the sample. The pulse reply signal may be further indicative of external or internal factors that have an influence of the measurement of the analyte. The pulse reply signal, as well as the electrical response signal in general, may be indicative of at least one of hematocrit, ascorbic acid, oxygen, humidity or temperature, just to mention a few.

In another example, the electrical response signal is analyzed during the entire measurement time interval and/or during time intervals between consecutive pulses of the sequence of pulses. With both approaches, an influence of a pulse-excitation of the sample and a pulse-excitation applied to the electrochemical reaction taking place on or with the sample can be monitored and analyzed.

According to another aspect, an analyte measurement device for measuring of an analyte in a sample is provided. The analyte measurement device comprises a signal generator configured to generate an electrical analysis signal, wherein the electrical analysis signal, when transferred into a frequency space, comprises a superposition of two or more non-zero frequency components at least at a sampling time. The analyte measurement device further comprises a controller connected to the electrical signal generator and electrically connectable to the sample. The controller is configured to measure at least one electrical response signal from the sample when the sample is exposed to the electrical analysis signal or when the electrical analysis signal is or has been applied to the sample.

The analyte measurement device is particularly configured to conduct the method of measuring an analyte as described above. Features and effects described above in relation to the method of measuring an analyte equally apply to the analyte measurement device and vice versa.

The controller may be also configured to analyze the electrical response signal and to determine the amount of the analyte in the sample on the basis of the analysis of the electrical response signal. Alternatively, the controller may be connected to a separate computing device, such as a computer or a smartphone having a computational unit or a processor configured to conduct the analysis and determination of the amount, the quantity or concentration of the analyte in the sample.

According to another example, the signal generator comprises a noise generator configured to generate at least one of a white noise frequency spectrum, a pink noise frequency spectrum, a red noise frequency spectrum, a blue noise frequency spectrum, a violet noise frequency spectrum and a grey noise frequency spectrum. The signal generator may be configured to constantly and to permanently apply a noise signal to the sample over the entire measurement time interval. Alternatively, the signal generator may be configured to apply the noise signal repeatedly at least during selected sampling times within the measurement time interval. The noise signal comprises a superposition of a multitude of frequency components, wherein each frequency component may be subject to temporal variations or fluctuations. It is even conceivable that the noise signal comprises an infinitesimal number of different frequency components. In this way, the sample can be simultaneously exposed to a large number or even to an infinitesimal number of different frequency components.

In another example, the analyte measurement device comprises a variable bandpass filter connected to the controller and tunable by the controller. The variable bandpass filter is configured to filter the electrical response signal returned from the sample in response to applying the electrical analysis signal to the sample. The variable bandpass filter is particularly configured to filter the electrical response signal when the electrical analysis signal applied to the sample comprises a noise signal, such as a pink noise frequency spectrum. By means of tuning the variable bandpass filter the controller is configured to select predefined frequency components of the electrical response signal during the measurement time interval. In this way, the controller fulfills a double function. In one aspect the controller is configured to select a center frequency and hence a particular frequency component. In a second aspect, the controller is configured to measure and to analyze the electrical response signal with regards to the selected frequency component or with regards to the selected or tuned center frequency of the variable bandpass filter.

According to a further example, the controller is configured to tune the variable bandpass filter to a first center frequency at a first sampling time and to measure or to record a portion of the electrical response signal filtered by the variable bandpass filter at the first sampling time. The control is further configured to tune or to adjust the variable bandpass filter to a second center frequency at a second sampling time and to measure or to record a portion of the electrical response signal filtered by the variable bandpass filter at the second sampling time. In this way, the controller and hence the analyte measurement device is capable to conduct a frequency selective analysis of the electrical response signal over time without modifying the electrical analysis signal applied to the sample.

According to another example the signal generator comprises a pulse generator configured to generate a sequence of pulses. The pulse generator is configured to generate a sequence of peak-shaped pulses or the pulse generator is configured to generate a sequence of rectangular-shaped pulses. Both different types of pulses as seen in the frequency space comprise a superposition of two or more non-zero frequency components. Typically, with a pulse generator as a signal generator the electrical response signal is analyzed either during the entire measurement time interval or during time intervals between consecutive pulses of the sequence of pulses generated by the signal generator. In this way, a dynamic reaction or response of the electrochemical reaction taking place on or at the sample can be monitored and analyzed to improve accuracy and reliability of the analyte measurement device.

According to another example the pulse generator and hence the signal generator comprises a current source configured to apply a rectangular-shaped current pulse to the sample. By means of a current source the sample can be charged or discharged in a controlled way. The charging or discharging of the sample by means of a rectangular shaped current pulse may be further indicative to internal or external factors. It may be also directly indicative of an amount, a quantity or a concentration of the analyte in the sample.

In a further example the analyte measurement device comprises a DC offset generator configured to apply a DC offset to the sample. By means of a DC offset, a basic measurement of the electrochemical reaction and a basic estimation of the amount, the quantity of concentration of the analyte in the sample can be conducted. The dynamic contributions to the electrical analysis signal, e.g. the sequence of pulses and the sample's pulse response may be exclusively of predominantly used to conduct a computational compensation of internal or external factors that may have a major impact on the measurement of the analyte in the sample.

According to a further example the controller is configured to deactivate the DC offset generator before activating the pulse generator to generate a sequence of pulses. The DC offset generator and the pulse generator may be operated concurrently so that only one of the DC offset generator and pulse generator is active at a given sampling time.

The above described method of measuring an analyte and the corresponding analyte measurement device may be predominantly configured for measuring blood glucose but are not limited to this application. In general, the method of measuring an analyte and the corresponding analyte measurement device may be configured to measure at least one of the following analytes: lactate, uric acid, ketones, creatinine, hemoglobin, total cholesterol, oxygen, carbon dioxide, proteins, sodium, potassium, calcium, magnesium, zinc, copper, iron, chromium, nickel or lead in a liquid biological sample, such as at least one of blood, urine and sweat.

The analyte measurement device may be implemented as a blood glucose monitoring device to measure a blood glucose concentration of a patient suffering a chronic disease, such as diabetes. The analyte measurement device may be used to determine an amount of a pharmaceutically active substance, hence a drug or medicament to be injected with a separate injection device. The analyte measurement device may be even implemented into an injection device.

The term "drug" or "medicament", as used herein, means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25]Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two µ sheets create a "sandwich" shape, held together by interactions between conserved cysteines and other charged amino acids.

There are five types of mammalian Ig heavy chain denoted by α, δ, ε, γ, and µ. The type of heavy chain present defines the isotype of antibody; these chains are found in IgA, IgD, IgE, IgG, and IgM antibodies, respectively.

Distinct heavy chains differ in size and composition; a and γ contain approximately 450 amino acids and δ approximately 500 amino acids, while µ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains µ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, embodiments of the drive mechanism and the injection device are described in detail by making reference to the drawings, in which.

DETAILED DESCRIPTION

In some electrochemical blood glucose monitoring (BGM) measurement schemes the measurement and the measurement results are affected by numerous external and internal factors. Internal factors may be an oxygen pressure in the sample, a level of hematocrit in the sample, or a level ascorbic acid in the sample. Humidity and temperature may be regarded as external factors that may have a substantial influence on the electrochemical analysis of the sample.

By means of elaborate calculations based on measurement signals and based on computational models some of these internal or external factors can be at least approximated, thus allowing to compensate the influence of at least one or some of such internal or external factors, e.g. a hematocrit interference on the measurement result.

Implementations of the present disclosure can provide an improved method of measuring an analyte in a sample and to provide an improved analyte measurement device for measuring such an analyte or several analytes in a sample. The improved method and the analyte measurement device may provide a rather robust, precise and failure safe measurement of an analyte in a sample. Furthermore, the analyte measurement device and the respective method should support computational compensation of external and internal factors having an influence on the measurement of the analyte.

Figure 1:
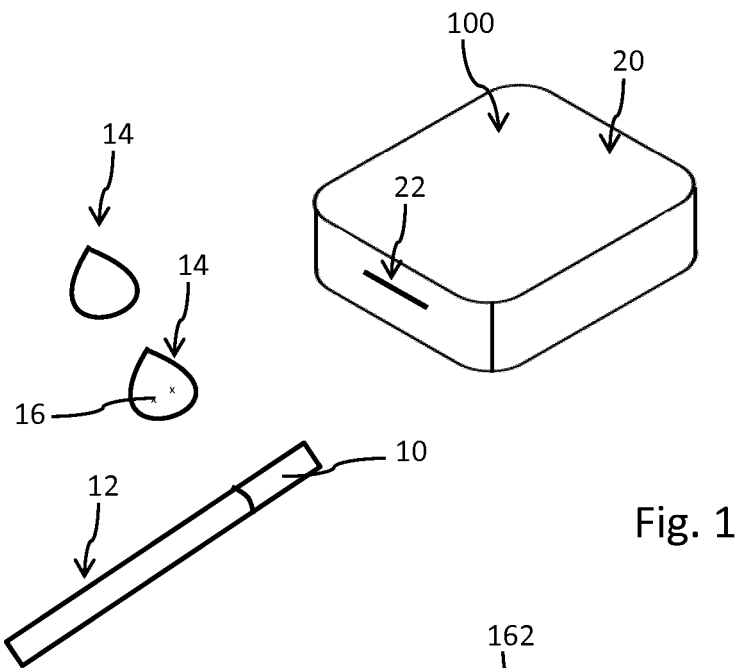
FIG. 1 is a schematic illustration of an analyte measurement device configured to measure an analyte in a sample.

In FIG. 1 an analyte measurement device 100 is schematically illustrated. The analyte measurement device 100 comprises a housing 20 and at least one receptacle 22 to receive a test strip 12. The test strip 12 is configured to receive a liquid medium, such as blood 14. When blood 14 is applied to the test strip 12 the test strip 12 converts into a biosensor or into a kind of an electrochemical cell. Typically and as described above, a test strip 12 comprises or is provided with numerous enzymes that start to react with the blood 14 as soon as blood 14 is applied to the test strip 12. The test strip 12 or at least a portion thereof is configured to receive a blood sample 14 and thus forms the sample 10 that is subject to electrochemical analysis to be conducted by the analyte measurement device 100. For this the receptacle 22 of the analyte measurement device 100 is formed to receive at least a portion of the test strip 12, namely that portion of the test trip 12 that carries the sample 10. The blood 14 applied to the test strip 12 comprises at least one analyte 16, e.g. blood glucose that is to be measured by the analyte measurement device 100.

Figure 5:
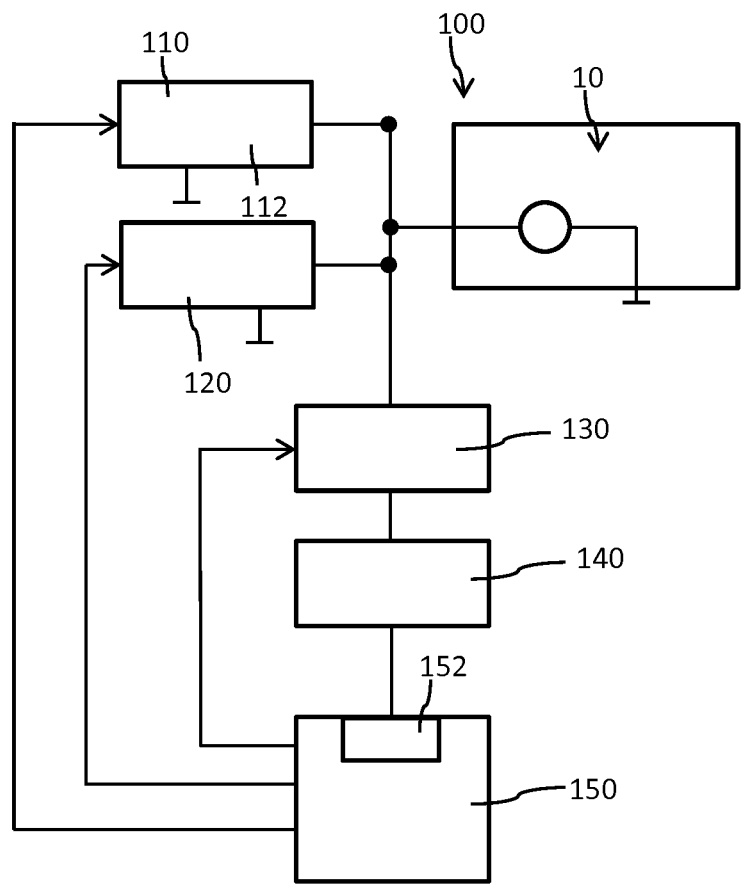
FIG. 5 shows a block diagram of one embodiment of an analyte measurement device.

The internal structure of the analyte measurement device 100 is schematically illustrated in FIG. 5. The analyte measurement device 20 comprises a controller 150 and a signal generator 110 both connected or connectable to the sample 10. In the present illustration the sample 10 is reproduced as an electrochemical cell. The sample 10 is electrically connected to the controller 150 as well as to the signal generator 110. The signal generator 110 and the controller 150 are connected in series. Moreover, the sample 10 is connected in series to the signal generator 110 and to the controller 150.

The analyte measurement device 100 may further comprise an optional DC offset generator 120 that is also connected in series to the signal generator 110, the sample 10 and to the controller 150. Between the sample 10 and the controller 150 there is arranged a variable bandpass filter 130. Between the variable bandpass filter 130 and the controller 150 there is arranged a rectifier and or integrator 140 by way of which a signal filtered by the variable bandpass filter 130 can be rectified and integrated to be further analyzed by the controller 150.

The controller 150 comprises an analog-to-digital converter 152. The controller 150 comprises a digital logic unit, such as a processor and a storage, e.g. a microcontroller, to conduct computational compensation of internal or external factors having an influence on the measurement.

The controller 150 is connected to the variable bandpass filter 130. The controller 150 is also connected to the signal generator 110. The controller 150 is configured to control and to tune the variable bandpass filter 130. The controller 150 is also configured to control and to operate the signal generator 110. The controller 150 is also connected to the DC offset generator 120. The controller 150 is configured to control, hence to activate or to deactivate the DC offset generator 120.

Between the signal generator 110 and the sample 10 there is arranged a resistor 114 acting as a reference resistor. The resistor 114 acts and behaves as a current to voltage converter.

Figure 2:
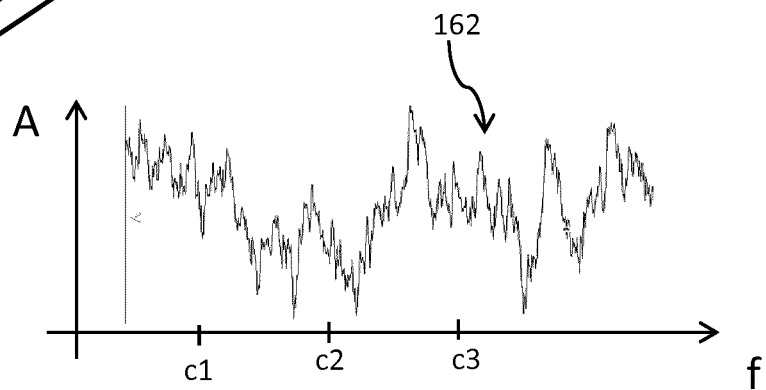
FIG. 2 is indicative of a spectrum of an example of an electrical analysis signal.
Figure 6:
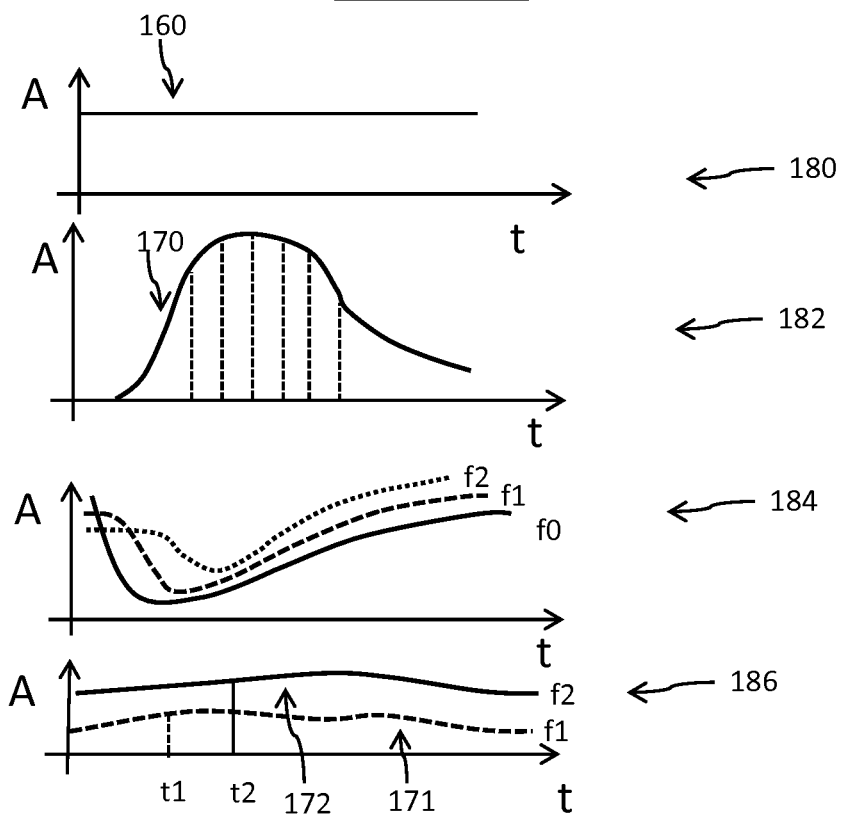
FIG. 6 is indicative of various amplitude diagrams of electrical analysis signals and of electrical response signals over time.

In the example as illustrated in FIG. 5 the signal generator 110 may be implemented as a noise generator 112 configured to generate a noise signal as an electrical analysis signal 160 as illustrated in FIG. 6. A frequency spectrum 162 of such a noise signal is shown in FIG. 2. The noise generator 120 is configured to generate a noise signal 160 as shown in the upper graph 180 of FIG. 6. The signal generator 110 and the noise generator thereof 112 is configured to generate a pink noise signal 160 as a continuous signal over time. Such a noise signal is applied as an electrical analysis signal 160 to the sample 10. After the electrochemical reaction on the test strip 12 has been activated by applying blood 14 thereto the sample 10 and the electrochemical cell produces an electrical response signal 170 as shown in graph 182 in FIG. 6. In all graphical representations of signals an amplitude A of the signal is given versus time or versus frequency. The amplitude signal A may represent one of a voltage, a current or an impedance.

The current and hence the electrical response signal generated by the sample 10 varies over time. In FIG. 6 the signals are illustrated over a measurement time interval MT. The measurement time interval MT may have a duration of a few seconds, e.g. 5 seconds to 10 seconds. It is apparent from the signal, that the response signal 170, hence a current generated by the sample 10 when activated with blood 14 increases and reaches a maximum after a significant portion of the measurement time interval MT. Thereafter and as time continues the current generated by the sample 10 slowly decreases.

In the graph 186 of the electrical response signal 170 there are illustrated two separate frequency components 171, 172 that are measured at sampling times t1 and t2. At these sampling times t1, t2 the electrical response signal 170 is measured by the controller 150. In the embodiment of FIG. 5 the noise generator 112 is configured to generate a noise signal 160 and to apply the noise signal to the sample 10. The frequency spectrum 162 of such this noise signal is for instance shown in FIG. 2. There, the amplitude of the noise signal over its frequency components is illustrated. It is apparent from FIG. 2, that the electrical analysis signal 160 comprises numerous frequency components c1, c2, c3, just to mention a few.

While the electrical analysis signal 160 in form of a noise signal is applied to the sample 10 continuously and over the entire measurement time interval MT the controller 150 is configured to tune the variable bandpass filter 130 to a series of different center frequencies f0, f1, f2. In particular, at a first sampling time t1 the bandpass filter 130 is tuned to a first center frequency f1. An electrical response signal 170 is then obtained from the sample 10. It is filtered by the variable bandpass filter 130 and a portion 171, hence a first frequency component 171 thereof that passes the variable bandpass filter 130 enters the rectifier and integrator 140. Thereafter, the rectified and integrated signal 171 is provided to the analog-to-digital converter 152 and is then analyzed by the controller 150. In this way and at the sampling time t1 the electrical response signal 170 is analyzed with regards to a frequency component with a center frequency f1. This is indicated in the graph 186 of FIG. 6.

At a second sampling time t2 the variable bandpass filter 130 is tuned to a second center frequency f2 by the controller 150. Then, another frequency component 172 of the broadband response signal 170 is filtered by the variable bandpass filter 130. Correspondingly, the rectifier and integrator 140 processes the filtered signal and provides a different signal to the analog-to-digital converter and hence to the controller 150.

The controller 150 is configured to repeatedly tune the variable bandpass filter 130 to numerous center frequencies and to measure a respective frequency component of the electrical response signal 170 for each center frequency of the electrical response signal that is received in response to applying the electrical analysis signal 160, hence the noise signal to the sample 10. The controller 150 is configured to repeatedly measure the electrical response signal 170 during the measurement time interval MT and to measure the electrical response signal 170 for each selected center frequency several times.

The controller 150 may conduct numerous measurement cycles during the measurement time interval MT, wherein during each measurement cycle a frequency component of the electrical response signal is only measured once. Each measurement cycle, hence a sweep over numerous frequency components of the electrical response signal 170 can be conducted at or during a sampling interval. So for each sampling interval each frequency component of the electrical response signal can be measured. By conducting numerous measurement cycles at numerous sampling times, a temporal evolution of frequency components of the electrical response signal can be derived.

In the graph 184 of FIG. 6 a temporal evolution of a complex impedance Z for three different frequency components f1, f2, f3 is given over the measurement time interval MT. From the temporal behavior of different frequency components f1, f2, f3 of the electrical response signal 170 internal and/or external factors influencing the measurement of the analyte can be compensated or calculated.

Typically, the variable bandpass sensor can be adjusted within a rather short time interval, e.g. within 500 ms, 100 ms, 10 ms or even faster. This leads to a sampling interval or sampling rate at which different frequency components of the electrical response signal can be selected and separately measured.

In the embodiment as shown in FIG. 5 the sample 10 comprises and represents a two pole electrochemical cell. Alternative, it could be implemented as a three pole cell further comprising a reference electrode.

Figure 7:
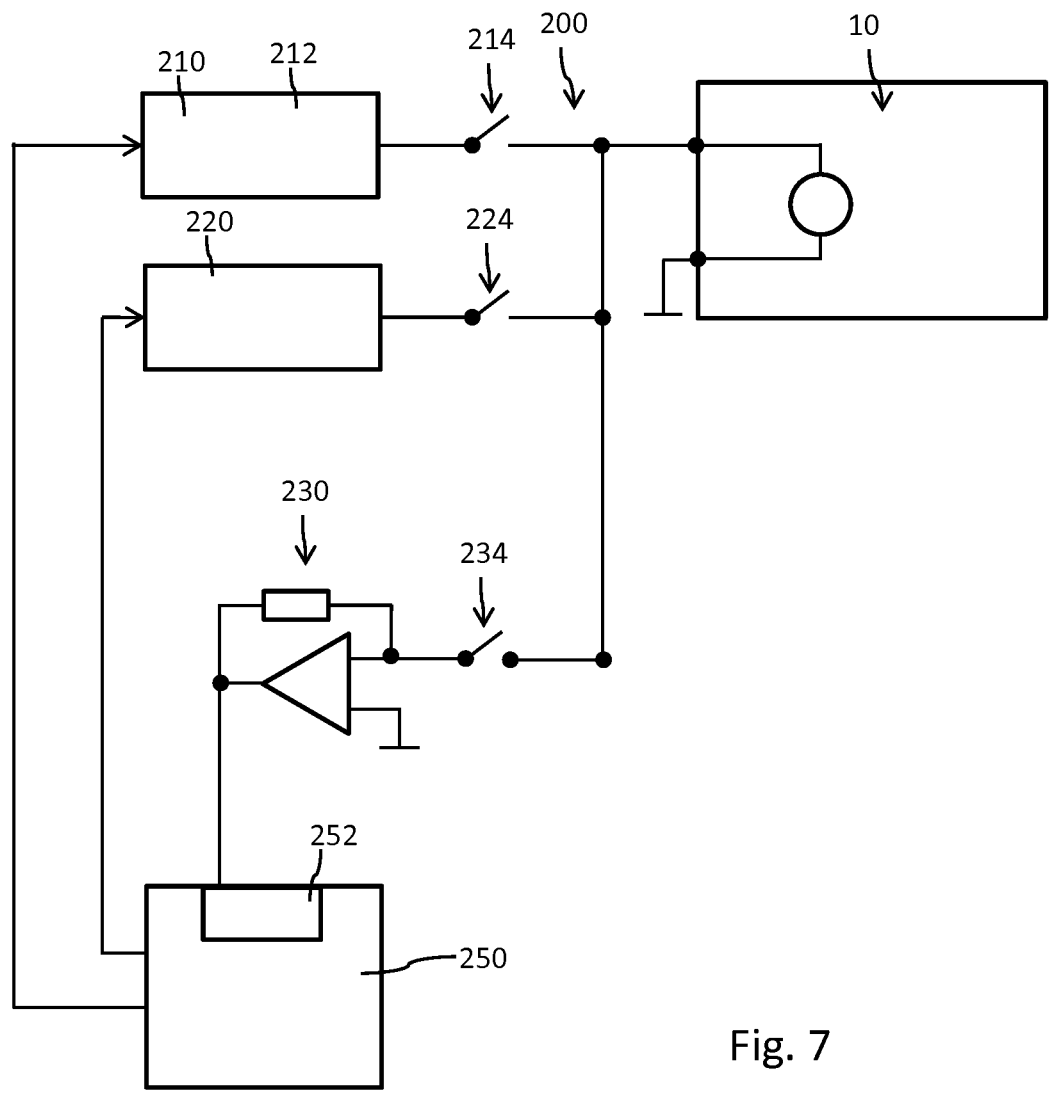
FIG. 7 shows a block diagram of another embodiment of an analyte measurement device.
Figure 8:
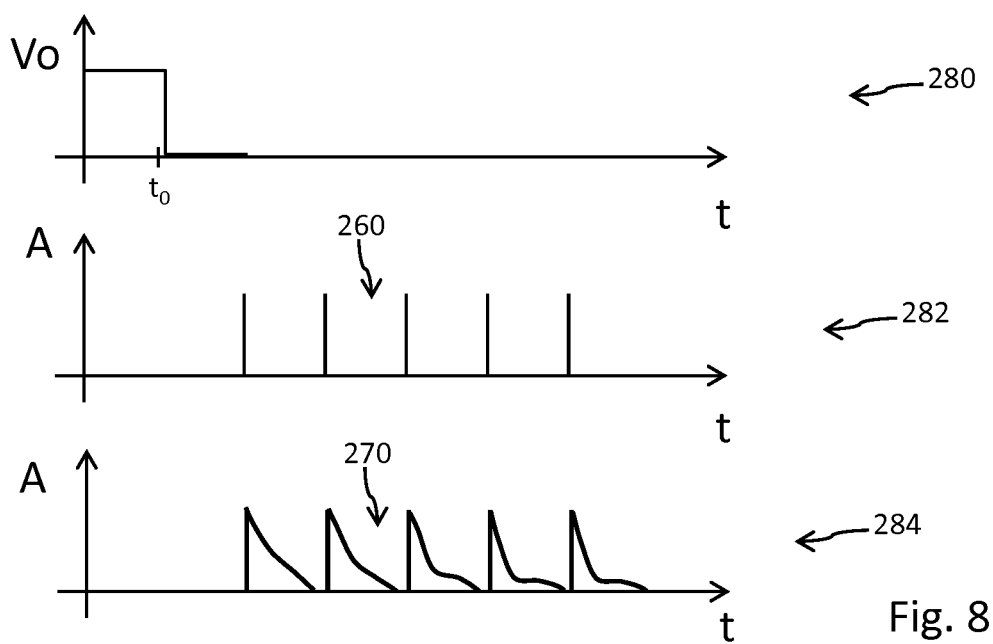
FIG. 8 is indicative of amplitude diagrams of an electrical analysis signal and of a corresponding electrical response signal over time.

The further example as shown in FIG. 7 and FIG. 8 uses a different type of signal generator 210. Here, the signal generator 210 comprises a pulse generator 212 configured to generate a sequence of peak-shaped pulses 260 as shown in FIG. 8. Also here, the controller 250 comprises and analog-to-digital converter 255. The controller 250 is connected to a DC offset generator 220 as well as to the signal generator 210. There are further illustrated switches 214, 224 and 234 that are also controllable by the controller 250. The switch 214 is located between the signal generator 210 and the sample 10. The switch 224 is connected parallel to the switch 214. The switch 224 is located between the DC offset generator 220 and the sample 10. The further switch 234 is connected parallel to the other two switches 214 and 224. By means of the switch 234, an amplifier 230 is connectable to one pole of the sample 10. An opposite end of the amplifier 230 is finally connected to the analog-to-digital converter 252 of the controller 250. The controller 250 may comprise a microcontroller so as to control operation of the DC offset generator 220 and of the signal generator 210. The controller 250 may be also configured to measure and to analyze the electrical response signal 270 obtainable from the sample 10.

The graph 280 of FIG. 8 shows the amplitudes or voltages generated by the DC offset generator 220 over time. At a time t0 the blood 14 is applied to a test strip 12. As a consequence, the sample 10 and the electrochemical cell represented by the sample 10 is electrochemically activated. As soon as activation of the electrochemical cell and hence as soon as activation of the sample is detected at the time t0 the controller 250 is configured to deactivate the DC offset generator 220. Here, the controller may detect the electrochemical activation of the sample 10. Thereafter or concurrently with the deactivation of the DC of the generator the controller 250 activates the signal generator 220. As shown in the graph 280 a sequence of peak-shaped pulses of a predefined voltage are applied as an electrical analysis signal 260 to the sample 10.

Thereafter and in time intervals between consecutive pulses the amplifier 230 is connected to the sample 10. Hence the switch 234 is closed during pulse-pauses. The amplifier 230 effectively provides a current to voltage converter and the amplifier 230 effectively forces the voltage at the terminals of the sample 10 to zero. Each pulse of the electrical analysis signal 260 in combination with the electromagnetic force generated by the electrochemical behavior of the sample 10 leads to a repeated current decay in the electrical response signal 270 which is monitored by the controller 250. The temporal behavior and the current decay of the electrical response signal 270 following a peak-shaped pulse of the electrical analysis signal 260 as shown in the graph 284 over time may be characteristic for at least one of the external or internal factors or for the concentration of the analyte in the sample.

By means of a specific algorithm taking into account various parameters such as the above-mentioned internal and external factors the analyte concentration or the amount or quantity of the analyte in the sample can be calculated. For this, a system of n-dimensional equations has to be solved. For solving such equations a neural network may be established by the controller 250 or the controller 250 may communicate with a separate computing device comprising such a neural network.

Figure 3:
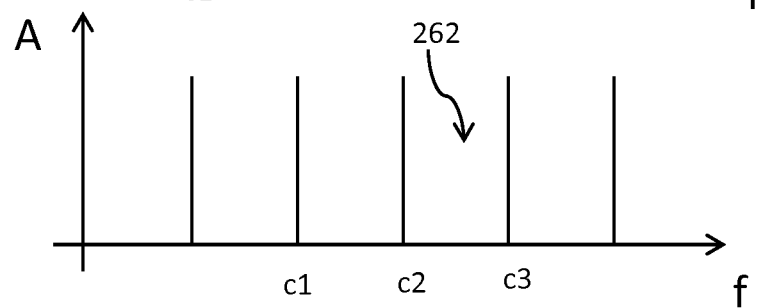
FIG. 3 is indicative of a spectrum of another example of an electrical analysis signal.

The series of peak-shaped pulses used as an electrical analysis signal 260 as shown in the time domain in the graph 282 of FIG. 8 is shown in the frequency domain as 262 in FIG. 3. The sequence of peak-shaped pulses may resemble or may comprise a so-called Dirac comb. It comprises numerous frequency components c1, c2, c3, which in superposition form a tempered distribution constructed from Dirac delta functions.

Figure 9:
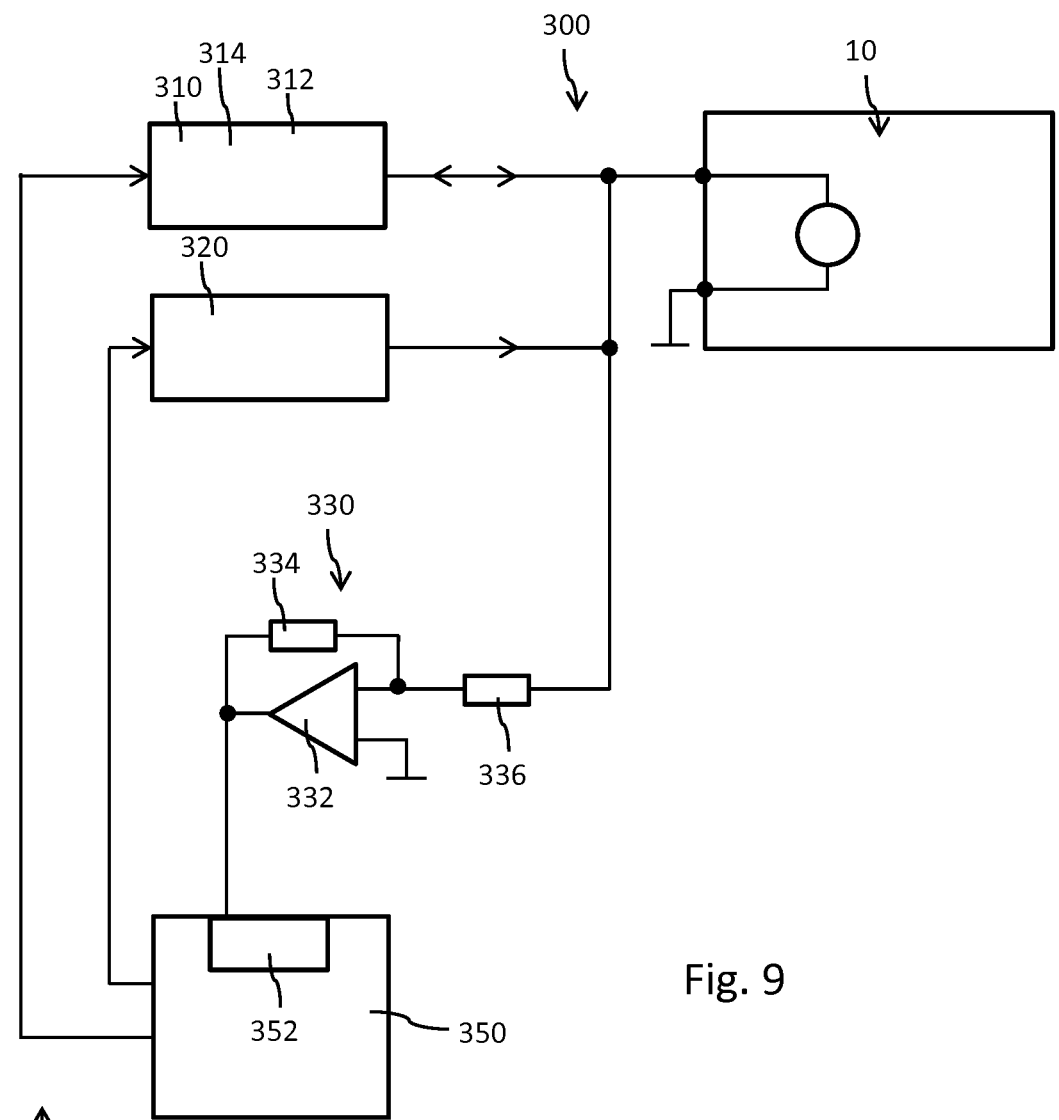
FIG. 9 shows a block diagram of a further embodiment of an analyte measurement device.
Figure 10:
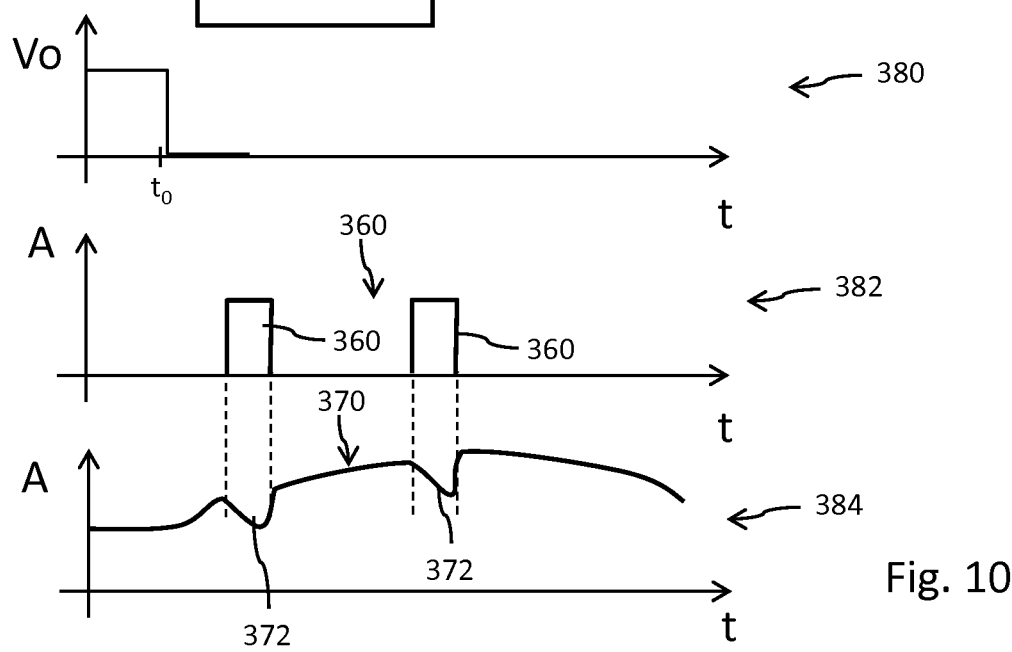
FIG. 10 is indicative of amplitude diagrams of an electrical analysis signal and of a corresponding electrical response signal over time.

In the further example as shown in FIGS. 9 and 10 a rectangular shaped pulse is applied as an electrical analysis signal 360 to the sample 10. The example according to FIG. 9 resembles the example according to FIG. 7. Here, the signal generator 310 also comprises a pulse generator 312 but contrary to the embodiment as shown in FIG. 7 the pulse generator 312 comprises a current source 314. The analyte measurement device 300 as shown in FIG. 9 also comprises a DC offset generator 320 that is connected in parallel to the signal generator 310. Both, the signal generator 310 and the DC offset generator 320 are connected in series to the sample 10 and hence to the electrochemical cell.

In parallel to the signal generator 310 and the DC offset generator 320 there is provided an amplifier 330. The amplifier 330 comprises an amplifying arrangement of an operational amplifier 332 and a resistor 334. The amplifier 330 is further provided with a separate resistor 336 to provide a current to voltage conversion. The resistor 336 is connected to an input of the amplifier 330. An input of the amplifier 330 is connected to the resistor 336, which is further connected to at least one pole or electrode of the sample 10. An output of the amplifier 330 is connected to an analog-to-digital converter 352 of the controller 350. The controller 350 is connected to the DC offset generator 320 as well as to the signal generator 310. The controller 350 is further configured to control the DC offset generator 320 as well as the signal generator 310.

In a similar way as described in connection to FIG. 7 and as the sample 10 is activated by receiving at least some drops of blood 14 a DC offset as shown in graph 370 is switched off at a time to. Here, activation of the sample 10 has been detected by the controller 350. Then and after a deactivation of the DC offset the controller 350 triggers application of the electrical analysis signal 360 to the sample 10.

Figure 4:
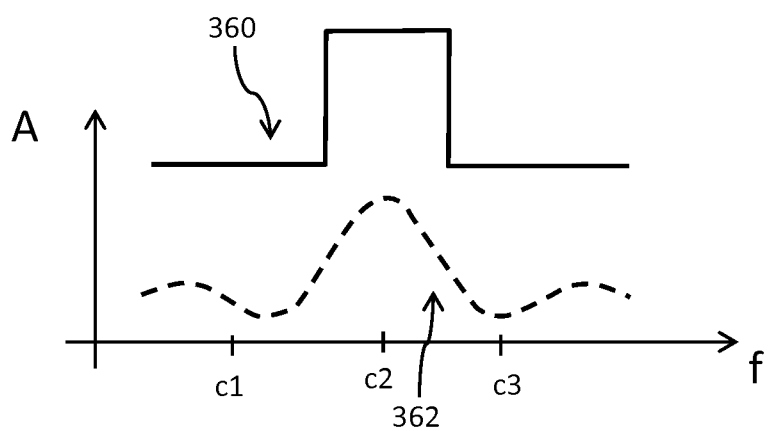
FIG. 4 is indicative of a spectrum of a further example of an electrical analysis signal.

Here, the electrical analysis signal 360 comprises a sequence of current pulses that are of rectangular shape in the time domain. In FIG. 4 the current pulse is represented in the time domain as 360 and its corresponding frequency spectrum is shown as 362. As shown there, the current pulse 360 comprises numerous frequency components c1, c2, c3 as illustrated in the corresponding frequency spectrum 362 of FIG. 4. Concurrently with the application of current pulses to the sample 10 a response of the sample 10 and hence an electrical response signal 370 reflected or produced by the sample 10 is measured by the controller 350. The sample 10 and the biosensor cell provided or formed by the sample 10 delivers a voltage and the current after it has been activated, e.g. by application of blood 14 onto the test strip 12.

By means of the current source 314 the sample 10 and hence the electrochemical cell is loaded and unloaded. During or after application of current pulses as shown in graph 382 to the sample 10 there evolve characteristic dips or modulations 372 in the amplitude of the electrical response signal 370 as shown in the graph 384. The size and the shape of the modulations 372 is indicative of internal or external factors having an influence on the measurement of the analyte in the sample 10. Moreover the size and shape of the modulations 372 can be indicative of the amount, the quantity and/or the concentration of the analyte 16 in the sample 10.

Figure 11:
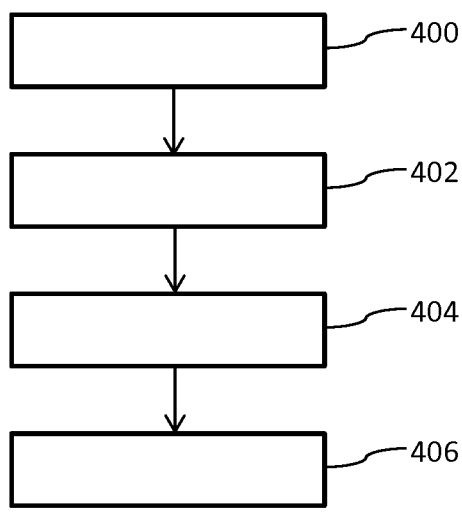
FIG. 11 shows a flowchart of a method of measuring an analyte in a sample.

In FIG. 11 a simple flowchart of the method of measuring an analyte 16 in a sample 10 is illustrated. In a first step 400, the sample is activated, e.g. by applying some drops of blood 14 onto a test strip 12 and by inserting the test strip 12 into an analyte measurement device 100 such as a BGM device. Then, in step 402 and electrical analysis signal 160 is applied to the sample 10. The electrical analysis signal 160 comprises a superposition of two or more non-zero frequency components at a sampling time when transferred into a frequency space.

During or after application of the electrical analysis signal 160 an electrical response signal 170 from the sample 10 is measured in step 404. Thereafter and in step 406 the electrical response signal is analyzed to determine an amount, a quantity or concentration of the analyte in the sample 10.

REFERENCE NUMBERS 10 sample
12 test strip 14 blood
16 analyte
20 housing
22 receptacle
100 analyte measurement device
110 signal generator
112 noise generator
114 resistor
120 DC offset generator
130 variable bandpass filter
140 rectifier
150 controller
152 analog-to-digital converter
160 electrical analysis signal
162 frequency spectrum
170 response signal
171 frequency component
172 frequency component
180 graph
182 graph
184 graph
186 graph
200 analyte measurement device
210 signal generator
212 pulse generator
214 switch
220 DC offset generator
224 switch
230 amplifier
234 switch
250 controller
252 analog-to-digital converter
260 electrical analysis signal
262 frequency spectrum
270 response signal
280 graph
282 graph
284 graph
286 graph
300 analyte measurement device
310 signal generator
312 pulse generator
314 current source
320 DC offset generator
330 amplifier
332 operational amplifier
334 resistor
336 resistor
350 controller
352 analog-to-digital converter
360 electrical analysis signal
362 frequency spectrum
370 response signal
372 modulation
380 graph
382 graph
384 graph

The invention claimed is:

1. A method of measuring an analyte in a sample, the method comprising:
applying an electrical analysis signal to the sample during a measurement time interval, wherein the electrical analysis signal is such that a transferred form of the electrical analysis signal in a frequency space comprises a superposition of two or more non-zero frequency components at least at one or more sampling times, and wherein the electrical analysis signal comprises a noise signal;
measuring at least one electrical response signal from the sample;
analyzing the electrical response signal; and
determining an amount of the analyte in the sample based on the analyzing.

2. The method according to claim 1, wherein the noise signal comprising at least one of: a white noise frequency spectrum, a pink noise frequency spectrum, a red noise frequency spectrum, a blue noise frequency spectrum, a violet noise frequency spectrum, or a grey noise frequency spectrum.

3. The method according to claim 1, wherein the electrical analysis signal comprises a sequence of pulses, wherein a single pulse of the sequence of pulses comprises a peak shaped pulse or a rectangular shaped pulse.

4. The method according to claim 3, wherein the electrical response signal is analyzed during the entirety of the measurement time interval or during time intervals between consecutive pulses of the sequence of pulses.

5. The method of claim 1, further comprising applying, in addition to the electrical analysis signal, a DC offset to the sample.

6. A method of measuring an analyte in a sample, the method comprising:
applying an electrical analysis signal to the sample during a measurement time interval, wherein the electrical analysis signal is such that a transferred form of the electrical analysis signal in a frequency space comprises a superposition of two or more non-zero frequency components at least at one or more sampling times;
measuring at least one electrical response signal from the sample;
analyzing the electrical response signal; and
determining an amount of the analyte in the sample based on the analyzing, wherein:
the electrical response signal is filtered by a variable bandpass filter, the variable bandpass filter comprising a center frequency that is varied during the measurement time interval, and
analyzing the electrical response signal comprises analyzing at least a portion of the electrical response signal that is filtered by the variable bandpass filter.

7. The method according to claim 6, wherein:
the one or more sampling times comprises a first sampling time and a second sampling time;
at the first sampling time, the variable bandpass filter is tuned to a first center frequency; and
at the second sampling time the variable bandpass filter is tuned to one or more second center frequencies that are different than the first center frequency.

8. The method according to claim 7, wherein the variable bandpass filter is repeatedly tuned to the first center frequency and to the one or more second center frequencies during the measurement time interval.

9. An analyte measurement device for measuring an analyte in a sample, the analyte measurement device comprising:
a signal generator comprising a noise generator configured to generate a noise signal as an electrical analysis signal, wherein the electrical analysis signal is such that a transferred form of the electrical analysis signal in a frequency space comprises a superposition of two or more non-zero frequency components at one or more sampling times; and a controller connected to the signal generator and electrically connectable to the sample, the controller configured to measure at least one electrical response signal from the sample when the sample is exposed to the electrical analysis signal.

10. The analyte measurement device according to claim 9, wherein the noise generator is configured to generate one or more of: a white noise frequency spectrum, a pink noise frequency spectrum, a red noise frequency spectrum, a blue noise frequency spectrum, a violet noise frequency spectrum or a grey noise frequency spectrum.

11. The analyte measurement device according to claim 9, further comprising a variable bandpass filter connected to the controller and tunable by the controller, wherein the variable bandpass filter is configured to filter the electrical response signal from the sample.

12. The analyte measurement device according to claim 11, wherein:

the controller is configured to:
tune the variable bandpass filter to a first center frequency at a first sampling time of the one or more sampling times;
measure or record a portion of the electrical response signal filtered by the variable bandpass filter at the first sampling time;
tune the variable bandpass filter to a second center frequency at a second sampling time of the one or more sampling times; and
measure or record a portion of the electrical response signal filtered by the variable bandpass filter at the second sampling time.

13. The analyte measurement device according to claim 9, wherein:

the signal generator comprises a pulse generator configured to generate a sequence of pulses; and
the pulse generator is configured to generate a sequence of peak shaped pulses or a sequence of rectangular shaped pulses.

14. The analyte measurement device according to claim 13, wherein the pulse generator comprises a current source configured to apply a rectangular shaped current pulse to the sample.

15. The analyte measurement device according to claim 9, further comprising a DC offset generator configured to apply, in addition to the electrical analysis signal, a DC offset to the sample.

16. The analyte measurement device according to claim 15, wherein the signal generator comprises a pulse generator configured to generate a sequence of pulses, and the controller is configured to deactivate the DC offset generator before activating the pulse generator to generate the sequence of pulses.

17. An analyte measurement device for measuring an analyte in a sample, the analyte measurement device comprising:

a signal generator configured to generate an electrical analysis signal, the electrical analysis signal comprising a sequence of pulses, and
being such that a transferred form of the electrical analysis signal in a frequency space comprises a superposition of two or more non-zero frequency components at one or more sampling times;
a controller connected to the signal generator and electrically connectable to the sample, the controller configured to measure at least one electrical response signal from the sample when the sample is exposed to the electrical analysis signal; and
a variable bandpass filter connected to the controller and tunable by the controller, the variable bandpass filter configured to filter the electrical response signal from the sample.

18. The analyte measurement device according to claim 17, wherein the sequences of pulses comprises one or more peak shaped pulses.

19. The analyte measurement device according to claim 17, wherein the sequences of pulses comprises one or more rectangular shaped pulses.

20. The analyte measurement device according to claim 17, wherein the controller is configured to:

tune the variable bandpass filter to a first center frequency at a first sampling time of the one or more sampling times;
measure or record a portion of the electrical response signal filtered by the variable bandpass filter at the first sampling time;
tune the variable bandpass filter to a second center frequency at a second sampling time of the one or more sampling times; and
measure or record a portion of the electrical response signal filtered by the variable bandpass filter at the second sampling time.

* * * * *